US010507069B2

(12) United States Patent
Ziegenspeck et al.

(10) Patent No.: US 10,507,069 B2
(45) Date of Patent: Dec. 17, 2019

(54) OPERATING DEVICE FOR A ROBOT-ASSISTED SURGICAL SYSTEM

(71) Applicant: avateramedical GmbH, Jena (DE)

(72) Inventors: Nils Ziegenspeck, Stuttgart (DE); Christian Trommer, Wipfratal (DE); Geralf Gude, Feldberger Seenlandschaft (DE); Thomas Schrumpf, Erfurt (DE); Andreas Karguth, Tüttleben (DE)

(73) Assignee: avateramedical GmbH, Jena (DE)

( * ) Notice: Subject to any disclaimer, the term of this patent is extended or adjusted under 35 U.S.C. 154(b) by 0 days.

(21) Appl. No.: 15/897,436

(22) Filed: Feb. 15, 2018

(65) Prior Publication Data

US 2018/0228560 A1    Aug. 16, 2018

(30) Foreign Application Priority Data

Feb. 16, 2017    (DE) .......................... 10 2017 103 199

(51) Int. Cl.
  *B25J 9/18*       (2006.01)
  *G05B 19/19*      (2006.01)
  *A61B 34/30*      (2016.01)
  *A61B 34/00*      (2016.01)
  *A61B 90/00*      (2016.01)

(52) U.S. Cl.
  CPC .............. *A61B 34/30* (2016.02); *A61B 34/70* (2016.02); *A61B 34/74* (2016.02); *A61B 2090/067* (2016.02)

(58) Field of Classification Search
  CPC ................................ A61B 34/40; A61B 34/70

USPC .................................................. 318/568.11
See application file for complete search history.

(56) References Cited

U.S. PATENT DOCUMENTS

| 6,424,885 | B1 | 7/2002 | Niemeyer et al. |
| 6,714,839 | B2 | 3/2004 | Salisbury, Jr. et al. |
| 6,799,065 | B1 | 9/2004 | Niemeyer |
| 2005/0065658 | A1* | 3/2005 | Green ................ A61B 1/00193 700/245 |
| 2009/0171374 | A1 | 7/2009 | Omori |
| 2010/0228265 | A1 | 9/2010 | Prisco |
| 2011/0301616 | A1 | 12/2011 | Sanchez et al. |

(Continued)

FOREIGN PATENT DOCUMENTS

EP    2740434 A1    6/2014

OTHER PUBLICATIONS

German Search report for counterpart application dated Oct. 16, 2017 (12 pages).

(Continued)

*Primary Examiner* — Erick D Glass
(74) *Attorney, Agent, or Firm* — Harness, Dickey & Pierce, P.L.C.

(57) ABSTRACT

An operating device (42) for a robot-assisted surgery system (10) comprising a manually actuatable operating element (124) as well as an interface (100) for attaching the operating device (42) to a holding unit (50). When attached to the holding unit (50), the operating element (124) is rotatable relative to the interface (100) about three axes of rotation (106, 114, 126) running orthogonally to each other, these three axes of rotation (106, 114, 126) intersecting in a common point of intersection (150).

19 Claims, 6 Drawing Sheets

(56) References Cited

U.S. PATENT DOCUMENTS

2016/0151115 A1     6/2016  Karguth et al.

OTHER PUBLICATIONS

Martin Glückler, et al. Miro-Lab. Nutzerorientierte Konzeption, 2012, (6 pages).
U.S. Appl. No. 14/951,965, filed Nov. 25, 2015, Andreas Karguth, et al.

* cited by examiner

OPERATING DEVICE FOR A ROBOT-ASSISTED SURGICAL SYSTEM

CROSS-REFERENCE TO RELATED APPLICATION

This application claims the benefit and priority of DE 10 2017 103 199.5, filed Feb. 6, 2017. The entire disclosure of the above application is incorporated hereby by reference.

FIELD

The invention relates to an operating device for a robot-assisted surgical system, comprising a manually actuatable operating element including two straps for receiving one finger of a user each, in particular for receiving the thumb and the middle finger of the user. Further, the operating device has an interface for attachment to a holding unit, the operating device, when attached to the holding unit via this interface, being rotatable relative to the interface about a first, a second and a third axis of rotation, these three axes of rotation being orthogonal to each other.

BACKGROUND

In minimally-invasive surgery, so-called telemanipulator systems, also referred to as robot-assistance systems or generally as apparatus for robot-assisted surgery, are increasingly used. By means of an apparatus for robot-assisted surgery, surgical instruments are controlled in their position and orientation on the basis of user inputs. The surgical instruments are further mechanically, electrically and/or optically coupled to the telemanipulator system so as to be able to implement an active positioning and orientation of the surgical instrument as well as a desired actuation of a surgical instrument. For this, the surgical instruments, which in addition to instruments with end effectors also comprise endoscopes and medical apparatuses to be operated, have a coupling interface which may be designed as a coupling unit and is also referred to as sterile unit. The apparatus for robot-assisted surgery further has at least one manipulator arm, at the proximal end of which the coupling unit is provided, to which the sterile unit is connectable in order to enable the mechanical, electrical and/or optical coupling between the manipulator arm and the surgical instrument.

SUMMARY

For controlling the telemanipulator system, operating devices are used which are arranged at a central control unit and by which the surgeon shall be enabled to control the surgical instruments attached to the robot arm as precisely as possible.

What is problematic with known operating devices is in particular that these often do not allow an intuitive movement of the surgical instruments, and in particular that the movement is not performed such as if the surgeon actually were to hold the surgical instrument directly in his/her hand. Usually, the reason for this is that the individual movement and rotation axes of the operating devices clearly differ from those of the human hand so that a movement differing from that of the hand is performed. This has the consequence that the surgeon always has to get used to the input devices and that, without sufficient training, the necessary precise control of the surgical instruments cannot be guaranteed.

It is an aspect of the invention to specify an operating device for a robot-assisted surgical system, by means of which the robot-assisted surgical system can be controlled as precisely as possible.

According to an aspect of the invention, the operating device is designed such that the three axes of rotation about which the operating element is rotatable intersect in a common point of intersection.

Here, this point of intersection in particular lies within the operating element, the point of intersection in particular being arranged between the two straps through which the fingers are passed. In particular, the point of intersection is arranged centrally between the two straps and preferably such that it coincides with the center of the operating element.

It turned out that by arranging the axes of rotation such that they intersect in a common point and in particular that this point is arranged between the straps and thus between the fingers of the surgeon, there results a particularly intuitive, easy control since the resulting grip and the movements sensed by the operating device intuitively correspond to those as if the surgeon directly were to hold the surgical instrument with his/her two fingers passed through the straps.

Strap in particular means any type of loop or other elements through which the fingers can be passed. In particular, the operating element is designed such that through the one strap the thumb of the surgeon and through the other strap the middle finger can be passed. In particular, the straps are formed from a flexible element, in particular a band.

In addition, the arrangement of the three axes of rotation such that they intersect in one point and this point lies within the operating element has the advantage that hereby the mass moment of inertia to be compensated and the parasitic forces are minimized, as a result whereof an even easier intuitive control is achieved.

The operating device in particular comprises a base element including the interface so that the operating device is attachable to the holding unit via this base element, this base element then being arranged on the holding unit in particular in a rotationally fixed manner. The holding unit can in particular be an arm of a stand, this arm in turn in particular being movable in a translational manner in up to three directions and in addition may be rotatable about a joint in up to three directions. Thus, it is achieved that an orientation in virtually any possible position within space is possible.

On the base element in particular a pivot unit is rotatably mounted, the mounting being such that the pivot unit is rotatably mounted relative to the base element about the first axis of rotation. On the pivot unit in turn, a housing is mounted rotatably relative to the pivot unit about the second axis, on this housing then in turn the operating element being mounted rotatably about the third axis of rotation. Via this chain of rotatable mountings, it is achieved that the operating element, which the surgeon holds in his/her hand for actuation, is rotatable relative to the interface about all three axes of rotation.

The movement performed by the surgeon on the operating element is in particular determined by means of sensors, the robot-assisted surgical system subsequently being controlled such that the surgical instruments held by it perform the previously determined movement.

In a particularly preferred embodiment of the invention, the operating element is formed disk-like, wherein disk-like in particular means an approximately cylindrical element, the diameter of which is greater than its thickness.

The two straps are in particular arranged oppositely to each other on both sides of the disk.

Such a disk-like element can be received within the hand of the surgeon in a particularly easy and ergonomically favorable manner, wherein in particular the inner surface of the hand rests on the circumferential surface of the operating element.

The housing in particular comprises two rings between which the disk-like operating element is arranged, the operating element being attached to the housing via bearings, in particular thin ring bearings, so that the operating element can be rotated relative to the housing about the third axis. In particular, the mounting is such that a rotation by 360 degrees is possible.

The housing in turn is rotatably mounted via a further bearing, in particular a ball bearing, preferably two thin ring bearings, on the pivot unit. Thus, also hereby, a rotation by 360 degrees relative to the pivot unit is achieved, which in connection with the mounting of the operating element enables that the operating element is rotatable relative to the pivot unit and thus also to the interface both about the second and about the third axis of rotation by 360 degrees.

The pivot unit in turn is rotatably mounted on the base element via at least one ball bearing, preferably two thin ring bearings.

Further, it is advantageous when the operating device comprises a first actor for rotating the pivot unit about the first axis, a second actor for rotating the housing about the second axis and/or a third actor for rotating the operating element about the third axis of rotation. By means of these actors, on the one hand, the operating element can be oriented in a preset zero position when the operating element has previously been moved out of this zero position. On the other hand, via these actors a so-called force feedback on the operating element can be realized. For this, the forces and/or torques acting on the surgical instruments during the surgery are in particular determined by sensors and fed back to the operating element via the actors so that the surgeon can experience resistances and forces of the surgical instruments and thus gets the feeling as if he were to directly hold the surgical instruments.

The actors are in particular motors, preferably electric motors. This makes a simple structure and a precise control possible.

The first actor is in particular arranged on the base element and preferably is coupled via a toothed belt drive with the pivot unit so that the base element can be rotated about the first axis of rotation.

The second actor is in particular arranged on the pivot unit and preferably coupled to the housing via a further toothed belt drive so that the housing can be rotated relative to the pivot unit about the second axis of rotation via the second actor.

The third actor, on the other hand, is in particular not arranged on the housing but on the operating element and is each time rotated together with this operating element. In this way it is achieved that the operating element can be arbitrarily rotated relative to the housing by 360°.

The third actor is in particular connected to the housing via a pinion and a crown gear so that a rotatability relative to the housing about the third axis of rotation is provided.

Further, the operating device in particular comprises a first sensor for determining the rotational position about the first axis of rotation, a second sensor for determining the rotational position about the second axis and/or a third sensor for determining the rotational position about the third axis, the information gained thereby in particular being used to control the robot system. In particular, the sensors may also be integrated each time in the respective actors or the sensors provided in the actors anyway may be used for this.

Further, it is alternatively possible that one sensor is used for determining the rotational position about several axes.

The operating device is in particular designed such that the operating element is rotatable both about the second and the third axis of rotation by 360°. In this way, it is achieved that an adjusting range as large as possible is guaranteed.

In a preferred embodiment of the invention, the operating element has a button, via which the user can control further functions of the robot-assisted surgical system. This operating element can in particular be designed as a sliding button and is in particular arranged on the circumferential surface of the disk-like operating element.

In particular, the sliding button is biased by means of an elastic element, for example a pressure spring, in a predetermined position and can be moved by the user against the spring force for actuation of a micro switch. By means of the restoring force, the button is again moved into its initial position after release.

Alternatively, instead of a button, for example also a switch or a push button can be provided for control.

The button, the switch or the push button can preferably be rotatable together with the straps arranged on both sides of the basic body of the operating element so that the surgeon can reach and actuate it easily at any time independent of the position of the straps.

In a particularly preferred embodiment, the two straps are attached to the disk-like basic body of the operating element such that by them some type of pincer grasp is formed, with which the surgeon has the possibility of spreading and closing his/her two fingers passed through the straps, and this movement is sensed by corresponding sensors and is taken into account when controlling the surgical instrument of the robot-assisted surgery system.

For this, the two straps can be pivoted away from each other in particular by a predetermined angle about predetermined points of rotation, the two straps in particular being coupled such that relative to a zero position they are always both opened by the same angle. This zero position is in particular that position in which the two surfaces of the disk-like operating element on which the straps are attached are oriented parallel to each other.

DRAWINGS

Further features and advantages result from the following description which explains the invention in more detail on the basis of embodiments in connection with the enclosed Figures.

DETAILED DESCRIPTION

Figure 1:
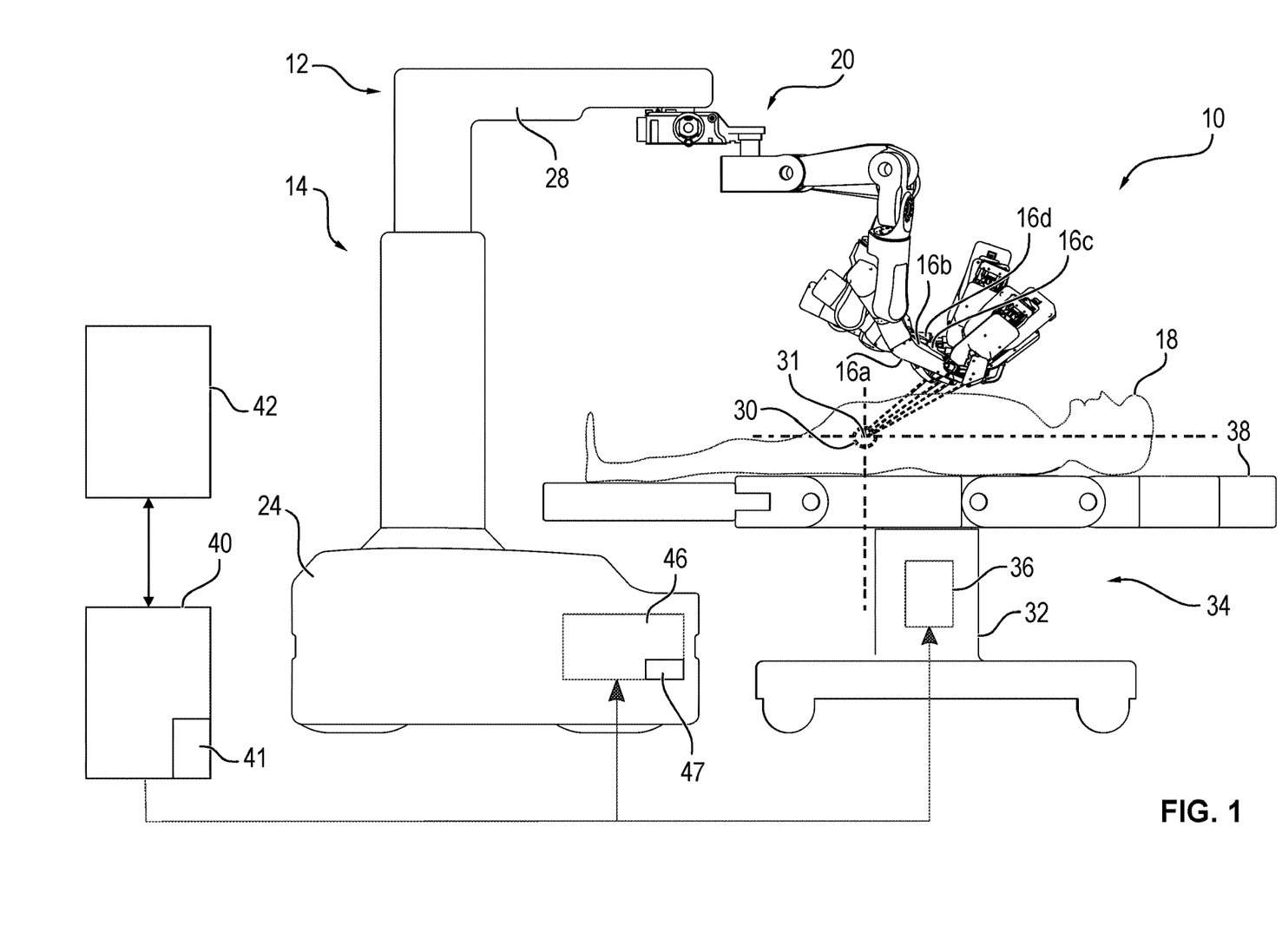
FIG. 1 shows a schematic side view of a system for robot-assisted surgery comprising a manipulator having four manipulator arms, to which one instrument unit each is connectable.

FIG. 1 shows a schematic side view of a system 10 for robot-assisted surgery with a manipulator 12 having a stand 14 and four manipulator arms 16a to 16d. The manipulator 12 is generally also referred to as apparatus for robot-assisted surgery. The system 10 serves to perform a surgery on a patient 18 positioned on an operating table 34. Based on the anatomy of the patient 18 and the surgery to be performed, the coordinates of a target surgical area 30 have been determined and stored in a preset manner. The stand 14 has an L-shaped stand arm 28, at the end of which that is remote from the stand base 24 the manipulator arms 16a to 16d are connected via a stand head 20.

The operating table 34 has an operating table column 32 in which a control unit 36 of the operating table 34 is arranged and on which a patient support surface 38 comprising several segments is arranged. The control unit 36 serves to control the movement of elements of the operating table 34, in particular for length adjustment of the operating table column 32 and thus for adjusting the height of the patient support surface 38 and for adjusting individual segments as well as the tilt and the swing of the patient support surface 38. Preferably, however, the adjustment of the segments of the operating table 34 is blocked during a surgery by means of the manipulator 12. The system 10 further comprises a control unit 46 of the manipulator 12 as well as a central control unit 40, the central control unit 40 being connected to the control unit 46 of the manipulator 12, the control unit 36 of the operating table 34 as well as a control panel 42 with a display unit 44 via data lines. The control unit 40 has an output unit 41 and the control unit 46 has an output unit 47, by each of which optical and/or acoustic signals can be output.

The surface of the patient support surface 38 forms a frontal plane on which the patient 18 is positioned in a dorsal manner.

Figure 2:
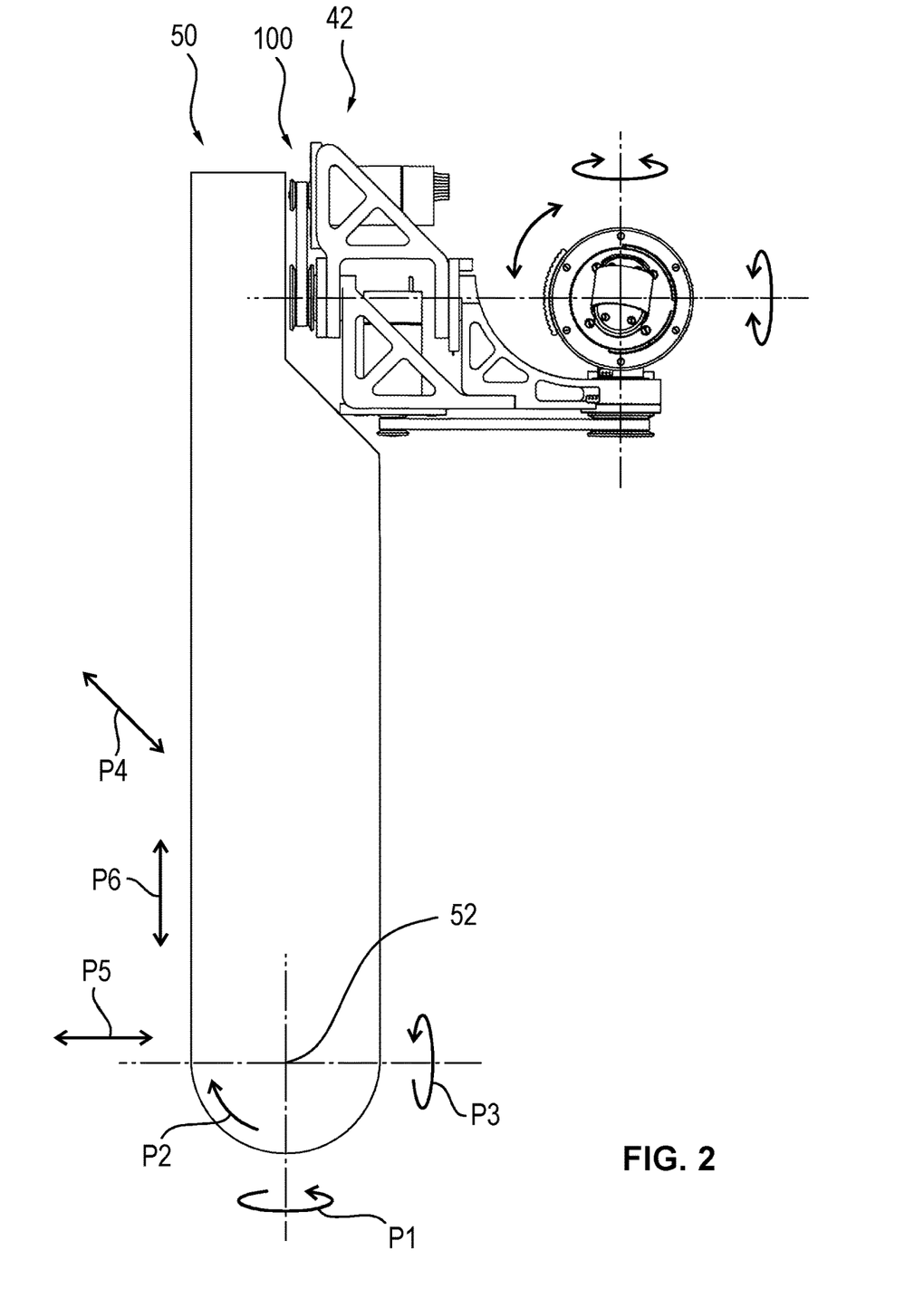
FIG. 2 shows a schematic illustration of an operating device for controlling the manipulator according to FIG. 2 as well as a holding unit to which the operating device is attached.

In FIG. 2, a schematic illustration of the operating device 42 as well as of a holding arm 50 to which the operating device 42 is attached via an interface 100 of the operating device is illustrated.

The holding arm 50 is rotatable around a point of rotation 52 as indicated by the arrows P1 to P3 about three axes which are orthogonal to each other. In addition, the holding arm 50 can be moved translationally in three directions that are orthogonal to each other, as indicated by the arrows P4 to P6. Thus, the operating device 42 can be oriented in an ergonomically favorable position for the user.

Figure 3:
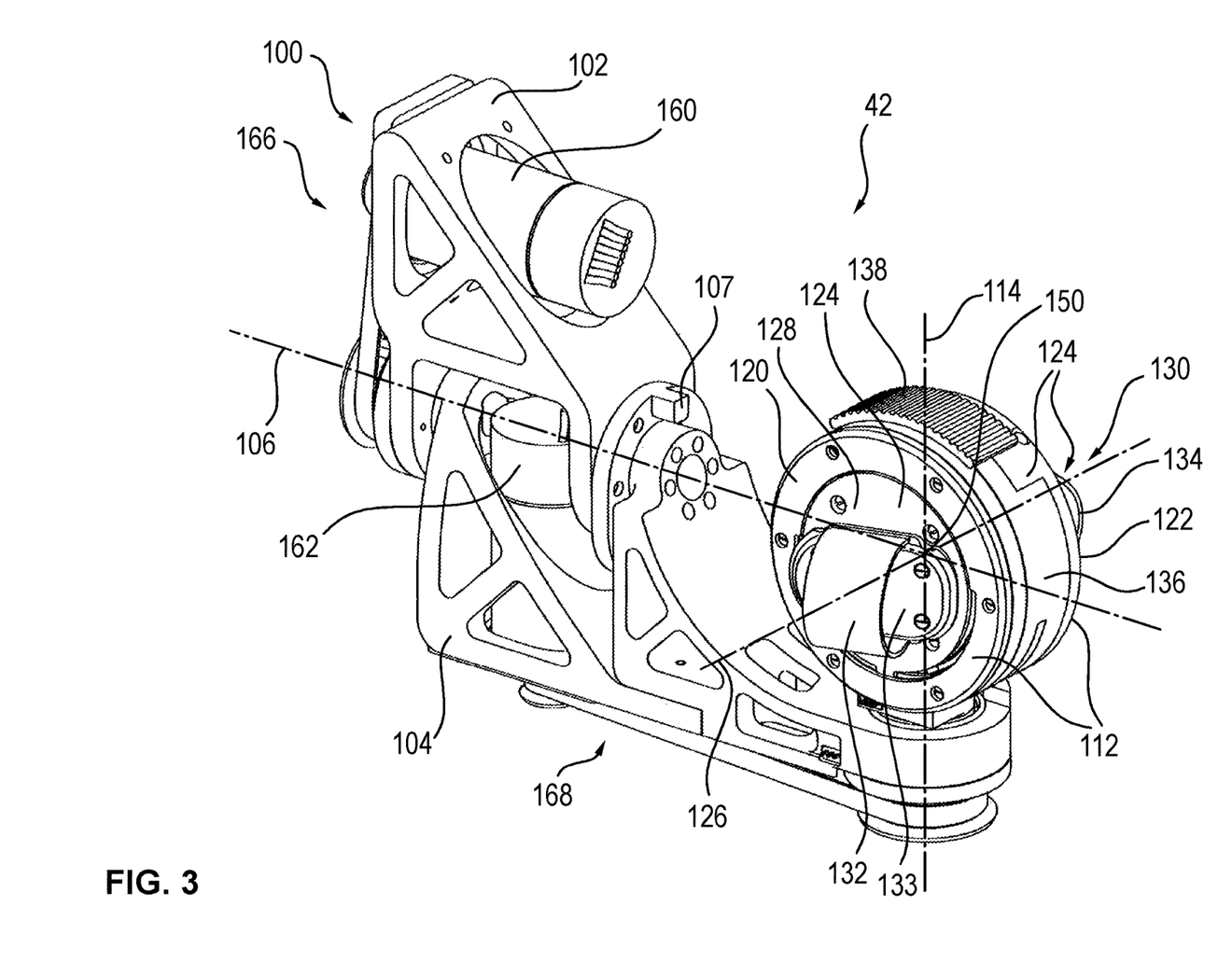
FIG. 3 shows a schematic perspective view of the operating device according to FIG. 2.
Figures 4, 5:
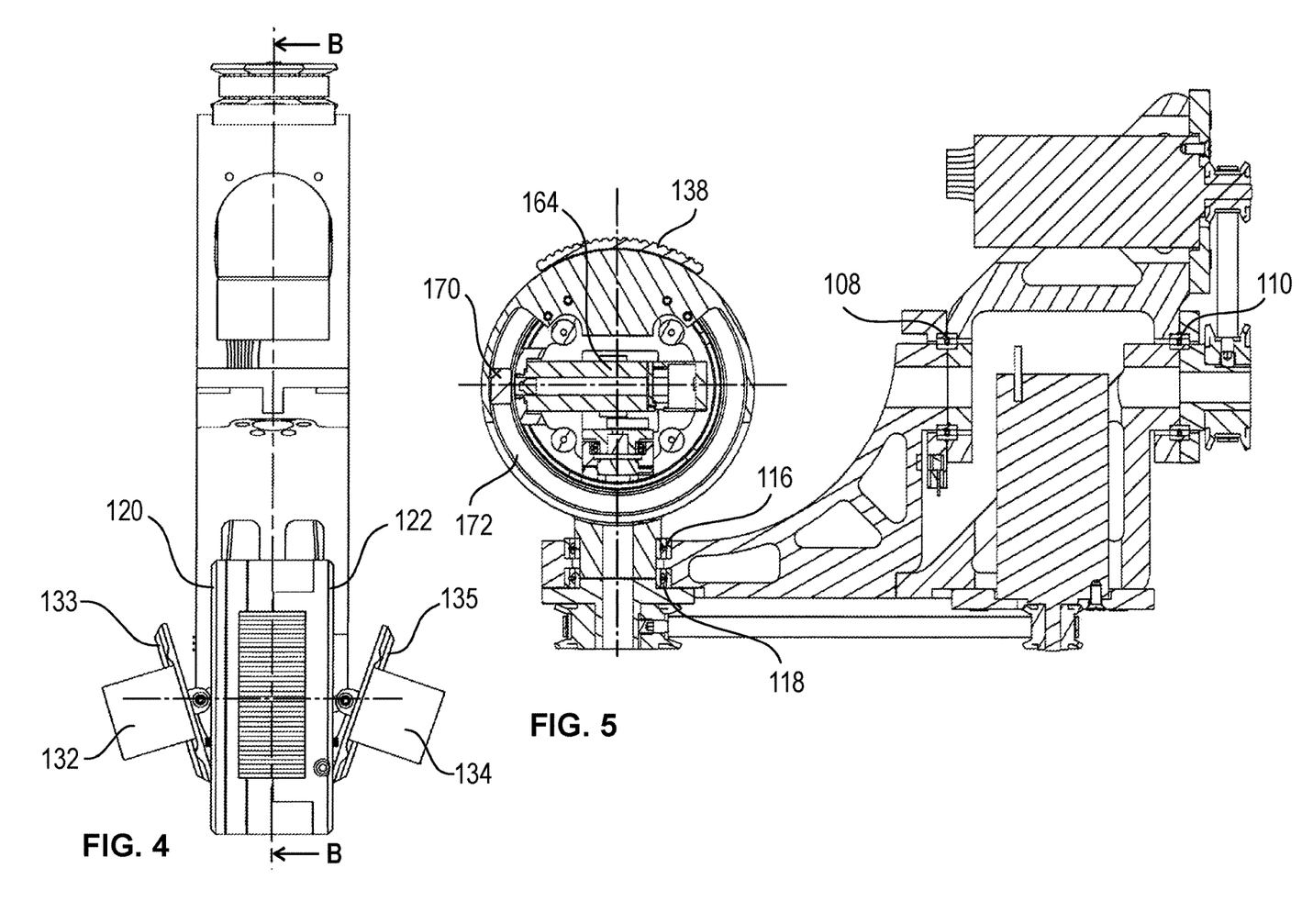
FIG. 4 shows a top view of the operating device according to FIGS. 2 and 3 with an open pincer grasp.
FIG. 5 shows a sectional view of the operating device according to FIGS. 2 to 4.

In FIG. 3, a schematic perspective illustration of the operating device 42 is shown. FIG. 4 shows a top view of the operating device and FIG. 5 shows a sectional view of the operating device 42 taken along the line B-B of FIG. 4.

The operating device 42 comprises a base element 102 on which the interface 100 is provided and via which the operating device 42 is attached to the holding arm 50. On the base element 102, a pivot unit 104 is rotatably mounted about a first axis of rotation 106. Here, the mounting takes place in particular via two thin ring bearings 108, 110.

At the end of the pivot unit 104 facing away from the base element 102 a housing 112 is arranged, which is mounted rotatably at the pivot unit 104 about a second axis of rotation 114. The rotatability is again achieved by the mounting of the housing via two thin ring bearings 116, 118.

The housing 112 comprises two rings 120, 122 between which a disk-like operating element 124 is arranged, this operating element 124 being rotatably mounted relative to the housing 112 and thus to the two rings 120, 122 about a third axis of rotation 126.

On both side surfaces 128, 130 of the disk-like basic body of the operating element 124, two straps 132, 134 are arranged through which the user can pass two fingers. In particular, the straps 132, 134 serve to receive the thumb and the middle finger. The straps 132, 134 are connected via pivotable pincer arms 133, 135 with one side surface 128, 130 each of the disk-like basic body of the operating element 124. On the circumferential surface 136 of the operating element 124, a sliding button 138 is provided which, when the operating element 124 is grasped as intended, is actuatable by the index finger resting thereon. The sliding button 138 can be connected to the operating element 124 such that a rotation of the operating element 124 about an axis of rotation 126 causes a rotation of the sliding button 138 by the same angle along the circumferential surface 136 so that the pincer arms 133, 135 and the sliding button 138 are in a fixed spatial relationship, as also results from a comparison of FIG. 2 with FIG. 3 or with FIG. 5.

Figure 6:
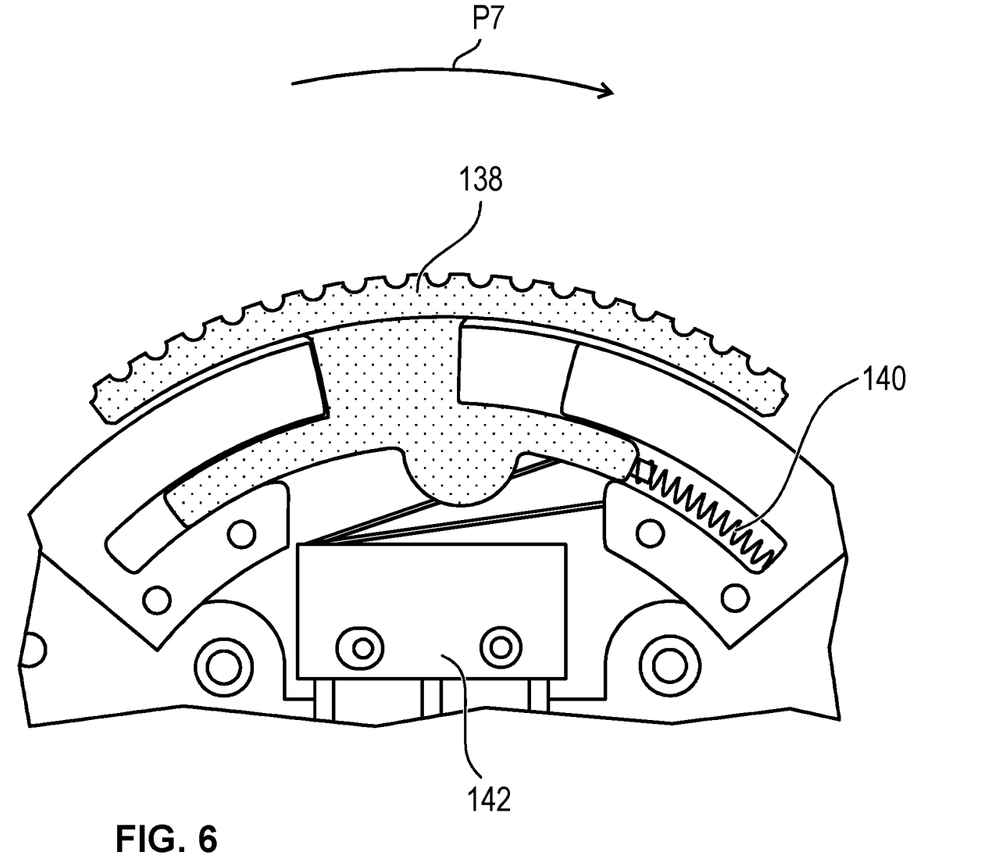
FIG. 6 shows a detail of a sectional view of an operating element of the operating device according to FIGS. 2 to 5, and FIGS. 7 and 8 each show a schematic illustration of a detail of the operating element.

As shown in FIG. 6, the sliding button 138 is biased in a first position via a pressure spring 140 and can be moved against the spring force of the pressure spring 140 in the direction of the arrow P7. Hereby, a miniature switch 142 is actuated, as a result whereof an associated function of the manipulator is triggered. After release of the sliding button 138, this button is moved back into the first position by the pressure spring 140.

The operating element 140 is thus rotatable about the three axes of rotation 106, 114 and 126, the three axes of rotation 106, 114, 126 each being oriented orthogonally to each other and intersecting in a common point of intersection 150. The range of rotation of the operating element 140 about each of the three axes 106, 114, 126 is preferably 360 degrees. In other embodiments, the range of rotation may also be restricted, for example to 90 degrees. This restriction may for example be effected by means of a stop 107.

By means of sensors, the respective rotational position of the operating element 124 with respect to the three axes 106, 114, 126 is determined and the manipulator is controlled such that the surgical instruments are moved accordingly.

By arranging the three axes of rotation 106, 114, 126 such that they intersect in a common point of intersection 150, a particularly intuitive control is made possible which gives the surgeon the feeling as if he/she were to hold the surgical instrument directly in the hand. This feeling is further supported by the fact that this point of intersection 150 lies within the operating element 124 between the two straps 132, 134 and in particular coincides with the center of the operating element 124. Further, in this way the mass moment of inertia to be compensated is minimized.

On the base element 102, a first actor is provided which via a first toothed belt drive 166 is coupled with the pivot unit 104 so that the pivot unit 104 can be rotated via this first actor 160 about the first axis of rotation 106.

On the pivot unit 104, in turn a second actor 162 is provided which is coupled with the housing 112 via a second toothed belt drive 168 so that the housing 112 can be rotated relative to the pivot unit 104 about the second axis of rotation 114.

Within the operating element 124 a third actor 164 is provided, which is connected to the operating element 124 in a rotationally fixed manner and is always moved together therewith. Via a pinion 170, the third actor 164 is engaged with a crown gear 172 which in turn is firmly connected to the housing 112. Via this, the operating element 124 can be rotated about the third axis of rotation 126 relative to the housing 112.

Via these three actors 160 to 164, thus on the one hand the operating element 124 can be oriented again in a preset zero position each time. On the other hand, a force feedback can be provided hereby, in which the forces and/or torques acting on the surgical instruments of the manipulator are determined and transmitted to the operating element via the actors 160 to 164 so that the surgeon receives a feedback about the manipulations made and thus a realistic surgery condition is modelled as if the surgeon were to directly hold the surgical instruments.

The two surfaces 128, 130 to which the straps 132, 134 are attached can be hinged down laterally relative to the other elements of the operating unit 124 and the housing 112, as shown in FIG. 4. In doing so, a pincer grasp is formed, the position of which is determined via sensors accordingly and is also transmitted to the control of the surgical instruments via the manipulator.

Figure 7:
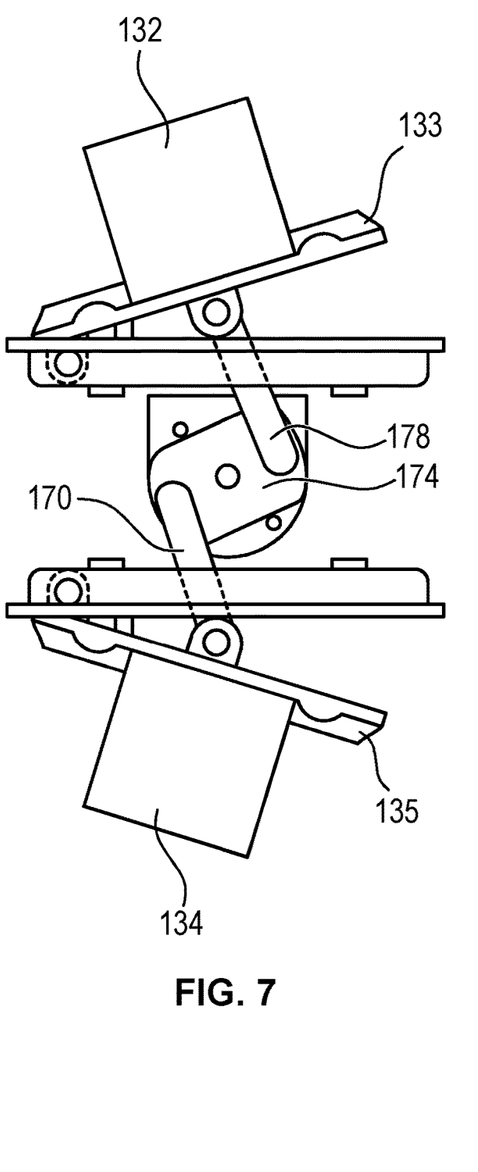
Figure 8:
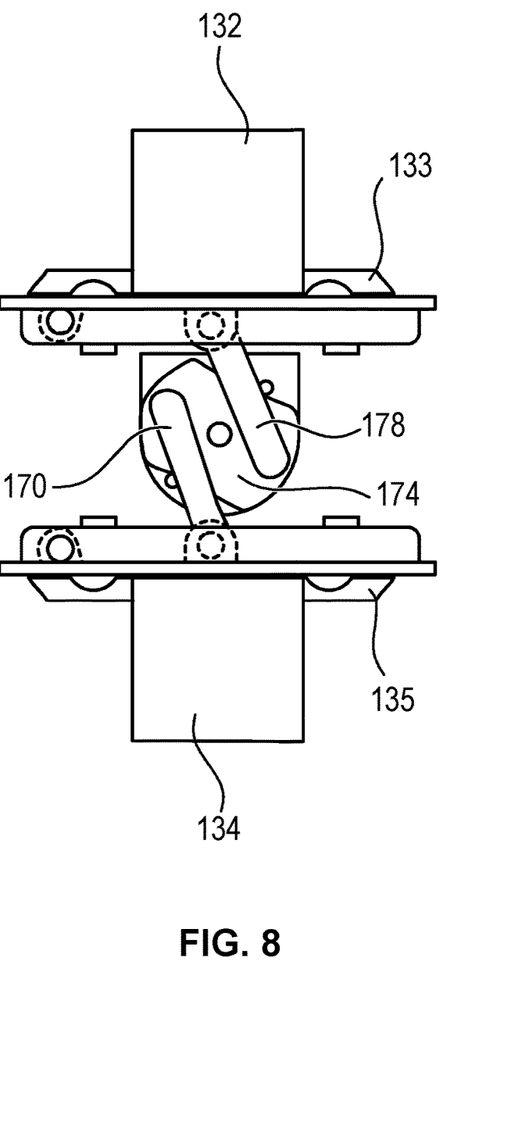

In FIG. 7 and FIG. 8, each time the two surfaces 128 and 130 and the two straps 132, 134 are shown, wherein in FIG. 8 the zero position in which the two surfaces 128 and 130 are oriented in parallel to each other, and in FIG. 7 the maximum opening of the pincer grasp is shown, in which each of the two surfaces 128, 130 is pivoted relative to the zero position in particular by a maximum angle of 17 degrees.

Each of the two straps 132, 134 is coupled via a rod 170, 178 to a rotatable disk 174, as a result whereof it is achieved that the two straps 132, 134 are always opened by the same angle relative to the zero position. Upon opening and closing of the pincer grasp a magnet of a Hall sensor coupled to the disk 174 is rotated, by which the respective angular position of the pincer grasp is determined and can be taken as a basis for controlling the manipulator.

LIST OF REFERENCE SIGNS

10 system
12 manipulator
14 stand
16, 16a to 16d manipulator arm
18 patient
20 stand head
24 stand base
28 stand arm
30 target surgical area
31 center of the target surgical area
32 operating table column
34 operating table
36 control unit of the operating table
38 patient support surface
40 central control unit of the apparatus
41 output unit
42 operating device
46 control unit of the manipulator
47 output unit
50 holding arm
52 point of rotation
100 interface
102 base element
104 pivot unit
106, 114, 126 axis of rotation
107 stop
108, 110, 116, 118 thin ring bearing
112 housing
120, 122 ring
124 operating element
128, 130 outer surface
132, 134 strap
133, 135 pincer arm
136 circumferential surface
138 sliding button
140 pressure spring
142 miniature switch
150 point of intersection
160, 162, 164 actor
166, 168 toothed belt drive
170 pinion
172 crown gear
174 disk
176, 178 rod
P1 to P7 direction

The invention claimed is:

1. An operating device for a robot-assisted surgery system, comprising;
a manually actuatable user operated element comprising two straps for receiving one finger of a user each; and
an interface for attaching the operating device to a holding unit;
wherein the user operated element, when the operating device is attached to the holding unit, is rotatable relative to the interface about a first axis of rotation, a second axis of rotation and a third axis of rotation, the three axes of rotation each being orthogonal to each other;
wherein the three axes of rotation intersect in a common point of intersection; and
wherein the user operated element includes a disk-like body.

2. The operating device according to claim 1, wherein the point of intersection lies within the user operated element.

3. The operating device according to claim 1, wherein the point of intersection lies between the two straps, in particular centrally between the two straps.

4. The operating device according to claim 1, wherein the point of intersection coincides with the center of the user operated element.

5. The operating device according to claim 1, wherein the operating device comprises a base element comprising the interface, a pivot unit mounted to the base element rotatably relative to the base element about the first axis of rotation, and a housing mounted to the pivot unit rotatably relative to the pivot unit about the second axis of rotation, and that the user operated element is mounted to the housing rotatably about the third axis of rotation.

6. The operating device according to claim 5, wherein the two straps are arranged on both sides of the basic body.

7. The operating device according to claim 5, wherein the housing comprises two rings between which the user operated element is arranged and that the user operated element is rotatably mounted to the housing via a thin ring bearing.

8. The operating device according to claim 5, wherein the housing is rotatably mounted to the pivot unit via at least one ball bearing, in particular two thin ring bearings.

9. The operating device according to claim 5, wherein the pivot unit is rotatably mounted to the base element via at least one ball bearing, in particular two thin ring bearings.

10. The operating device according to claim 5, wherein a first actor, in particular a first motor, is provided for rotating the pivot unit about the first axis of rotation, a second actor, in particular a second motor, is provided for rotating the housing about the second axis of rotation, and/or a third actor, in particular a third motor, is provided for rotating the user operated element about the third axis of rotation.

11. The operating device according to claim 10, wherein the first actor is arranged on the base element, that the second actor is arranged on the pivot unit and/or that the third actor is arranged on the user operated element.

12. The operating device according to claim 10, wherein the third actor is arranged inside the user operated element in a rotationally fixed manner relative to the user operated element.

13. The operating device according to claim 12, wherein the third actor is connected to the housing via a pinion and a crown gear.

14. The operating device according to claim 1, wherein a first sensor for determining the rotational position about the first axis of rotation, a second sensor for determining the rotational position about the second axis and/or a third sensor for determining the rotational position about the third axis of rotation are provided.

15. The operating device according to claim 1, wherein the user operated element is rotatable about the second axis of rotation and/or the third axis of rotation by 360° each.

16. The operating device according to claim 1, wherein the user operated element comprises a button, in particular a sliding button.

17. The operating device according to claim 16, wherein the button is rotatable together with the straps arranged on both sides of the basic body of the user operated element.

18. The operating device according to claim 1, wherein the two straps are pivotable towards each other by a predetermined angle so that a tweezers grasp is formed.

19. The operating device according to claim 18, wherein the two straps are coupled to each other such that they are always opened by the same angle relative to a zero position.

* * * * *